(12) United States Patent
Garcia Molina

(10) Patent No.: US 11,344,253 B2
(45) Date of Patent: May 31, 2022

(54) SYSTEM AND METHOD FOR DETERMINING SLEEP STAGE BASED ON SLEEP CYCLE

(71) Applicant: KONINKLIJKE PHILIPS N.V., Eindhoven (NL)

(72) Inventor: Gary Nelson Garcia Molina, Madison, WI (US)

(73) Assignee: KONINKLIIKE PHILIPS N.V., Eindhoven (NL)

(*) Notice: Subject to any disclaimer, the term of this patent is extended or adjusted under 35 U.S.C. 154(b) by 558 days.

(21) Appl. No.: 15/101,008

(22) PCT Filed: Dec. 3, 2014

(86) PCT No.: PCT/IB2014/066556
§ 371 (c)(1),
(2) Date: Jun. 2, 2016

(87) PCT Pub. No.: WO2015/092591
PCT Pub. Date: Jun. 25, 2015

(65) Prior Publication Data
US 2016/0296164 A1 Oct. 13, 2016

Related U.S. Application Data

(60) Provisional application No. 61/916,383, filed on Dec. 16, 2013.

(51) Int. Cl.
*A61B 5/00* (2006.01)
*A61B 5/291* (2021.01)
(Continued)

(52) U.S. Cl.
CPC .......... *A61B 5/4812* (2013.01); *A61B 5/369* (2021.01); *A61B 5/7278* (2013.01); *A61B 5/7282* (2013.01)

(58) Field of Classification Search
None
See application file for complete search history.

(56) References Cited

U.S. PATENT DOCUMENTS 6,658,287 B1* 12/2003 Litt ............... A61B 5/0476
600/544
2006/0293608 A1* 12/2006 Rothman ........ A61B 5/0476
600/545
(Continued)

FOREIGN PATENT DOCUMENTS

CN 102247122 A 11/2011
JP 2011122732 A 6/2011
(Continued)

OTHER PUBLICATIONS

Salih Gunes, Efficient sleep stage recognition system based on EEG signal using k-means clustering based feature weighing, 2010, Expert Systems with Applications, 37, pp. 7922-7928.*
(Continued)

*Primary Examiner* — Christine H Matthews
*Assistant Examiner* — Joshua Daryl D Lannu

(57) ABSTRACT

The present disclosure pertains to a system and method for determining sleep stages during individual sleep cycles based on algorithms and/or parameters that correspond to the individual sleep cycles. The system enables more accurate real-time sleep stage determinations compared to prior art systems. Sleep cycles are detected in real-time based on an electroencephalogram (EEG), and/or by other methods. At the end of a sleep cycle, the system is configured such that the specific algorithms and/or parameters used for the previous sleep cycle to determine sleep stages are replaced by new ones which are specifically adapted for the next sleep cycle.

14 Claims, 4 Drawing Sheets

(51) Int. Cl.
 *A61B 5/25* (2021.01)
 *A61B 5/369* (2021.01)

(56) References Cited

U.S. PATENT DOCUMENTS

| | | | | |
|---|---|---|---|---|
| 2007/0016095 | A1* | 1/2007 | Low | A61B 5/048 600/544 |
| 2008/0154111 | A1* | 6/2008 | Wu | A61B 5/0478 600/383 |
| 2008/0306351 | A1* | 12/2008 | Izumi | A61B 5/113 600/300 |
| 2008/0319505 | A1 | 12/2008 | Boyden et al. | |
| 2010/0049008 | A1* | 2/2010 | Doherty | A61M 16/024 600/301 |
| 2010/0240982 | A1 | 9/2010 | Westbrook et al. | |

FOREIGN PATENT DOCUMENTS

| | | |
|---|---|---|
| JP | 2013220314 A | 10/2013 |
| WO | 2006008743 A2 | 1/2006 |

OTHER PUBLICATIONS

K. Susmakova, Classification of Waking, Sleep Onset and Deep Sleep by Single Measures, 2007, Measurement Science Review, vol. 7, pp. 34-38.*

Theus H. Aspiras, Log Power Representation of EEG Spectral Bands for the Recognition of Emotional States of Mind, 2011, IEEE, pp. 1-5.*

Anderer et al, "An E-Health Solution for Automatic Sleep Classification According To Rechtschaffen and Kales: Validation Study of the Somnolyzer 24 7 Utilizing the Siesta Database", Neuropsychobiology, vol. 51, 2005, pp. 115-133.

Pracka et al, "Spectral Analysis in Cyclic Changes of Human Sleep Evaluation", Acta Neurobiologiae Experimentalis, 1996, p. 255.

Ngo, "Auditory Closed-Loop Stimulation of the Sleep Slow Oscillation Enhances Memory", Neuron, vol. 78, 2013 pp. 545-553.

Riedner et al, "Enhancing Sleep Slow Waves With Natural Stimuli," Medicamundi, vol. 45, No. 2, pp. 82-88, 2010.

Landsness et al, "Antidepressant Effects of Selective Slow Wave Sleep Deprivation in Major Depression: A High-Density Eeg Investigation.," Journal of Psychiatric Research, vol. 15, No. 8, pp. 1019-1026, Aug. 2011.

Antonenko et al, "Napping To Renew Learning Capacity: Enhanced Encoding After Stimulation of Sleep Slow Oscillations.," the European Journal of Neuroscience, vol. 37, pp. 1142-1151, Jan. 2013.

Garcia-Molina et al, "Online Single Eeg Channel Based Automatic Sleep Staging," In in Engineering Psychology and Cognitive Ergonomics. Applications and Services, vol. 8020, 2013, pp. 333-342.

Berezhnoy et al, "Towards Unobtrusive Automated Sleep Stage: Polysomnography Using Electrodes On the Face," In Healthinf 2012; Int. Conf. On Health Informatics, 2012, pp. 187-492.

* cited by examiner

SYSTEM AND METHOD FOR DETERMINING SLEEP STAGE BASED ON SLEEP CYCLE

CROSS-REFERENCE TO PRIOR APPLICATIONS

This application is the U.S. National Phase application under 35 U.S.C. § 371 of International Application Serial No. PCT/IB2014/066556, filed on Dec. 3, 2014, which claims the benefit of U.S. Application Ser. No. 61/916,383, filed on Dec. 16, 2013. These applications are hereby incorporated by reference herein.

BACKGROUND

Field

The present disclosure pertains to a system and method for determining sleep stages during individual sleep cycles based on algorithms and/or parameters that correspond to the individual sleep cycles.

Description of the Related Art

Systems for monitoring sleep are known. Determining sleep stages during sleep is known. Typically, sleep stages are determined based on a static sleep stage determination method that does not change as a subject progresses through a sleep session. Static sleep stage determination methods typically process polysomnography signals under an implicit assumption that the patterns in the signals remain stable throughout a night of sleep. This assumption permits the use of simpler sleep stage determination methods. However, these methods can only roughly estimate a subject's sleep stage.

SUMMARY

Accordingly, one or more aspects of the present disclosure relate to a system configured to determine sleep stages of a subject during individual sleep cycles of a sleep session. The system comprises one or more sensors, one or more physical computer processors, and/or other components. The one or more sensors are configured to generate output signals conveying information related to brain activity of the subject. The one or more physical computer processors are configured to perform various activities by computer readable instructions. The one or more physical computer processors are configured to detect individual sleep cycles during the sleep session based on the output signals, the individual sleep cycles including a first sleep cycle and a second sleep cycle. The one or more physical computer processors are configured to obtain sleep stage detection algorithms and/or parameters that correspond to different detected sleep cycles, the sleep stage algorithms and/or parameters including first algorithms and/or parameters that correspond to the first sleep cycle and second algorithms and/or parameters that correspond to the second sleep cycle. The one or more physical computer processors are configured to determine sleep stages during different detected sleep cycles based on the output signals and the obtained sleep stage detection algorithms and/or parameters for the corresponding sleep cycles such that, during the first sleep cycle, sleep stages are determined based on the output signals and the first algorithms and/or parameters, and, during the second sleep cycle, sleep stages are determined based on the output signals and the second algorithms and/or parameters.

Another aspect of the present disclosure relates to a method for determining sleep stages of a subject during individual sleep cycles of a sleep session with a sleep stage determination system. The system comprises one or more sensors, one or more physical computer processors, and/or other components. The method comprises generating, with the one or more sensors, output signals conveying information related to brain activity of the subject; detecting, with the one or more physical computer processors, individual sleep cycles during the sleep session based on the output signals, the individual sleep cycles including a first sleep cycle and a second sleep cycle; obtaining, with the one or more physical computer processors, sleep stage detection algorithms and/or parameters that correspond to different detected sleep cycles, the sleep stage algorithms and/or parameters including first algorithms and/or parameters that correspond to the first sleep cycle and second algorithms and/or parameters that correspond to the second sleep cycle; and determining, with the one or more physical computer processors, sleep stages during different detected sleep cycles based on the output signals and the obtained sleep stage detection algorithms and/or parameters for the corresponding sleep cycles such that, during the first sleep cycle, sleep stages are determined based on the output signals and the first algorithms and/or parameters, and, during the second sleep cycle, sleep stages are determined based on the output signals and the second algorithms and/or parameters.

Still another aspect of the present disclosure relates to a system configured to determine sleep stages of a subject during individual sleep cycles of a sleep session, the system comprising means for generating output signals conveying information related to brain activity of the subject; means for detecting individual sleep cycles during the sleep session based on the output signals, the individual sleep cycles including a first sleep cycle and a second sleep cycle; means for obtaining sleep stage detection algorithms and/or parameters that correspond to different detected sleep cycles, the sleep stage algorithms and/or parameters including first algorithms and/or parameters that correspond to the first sleep cycle and second algorithms and/or parameters that correspond to the second sleep cycle; and means for determining sleep stages during different detected sleep cycles based on the output signals and the obtained sleep stage detection algorithms for the corresponding sleep cycles such that, during the first sleep cycle, sleep stages are determined based on the output signals and the first algorithms and/or parameters, and, during the second sleep cycle, sleep stages are determined based on the output signals and the second algorithms and/or parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
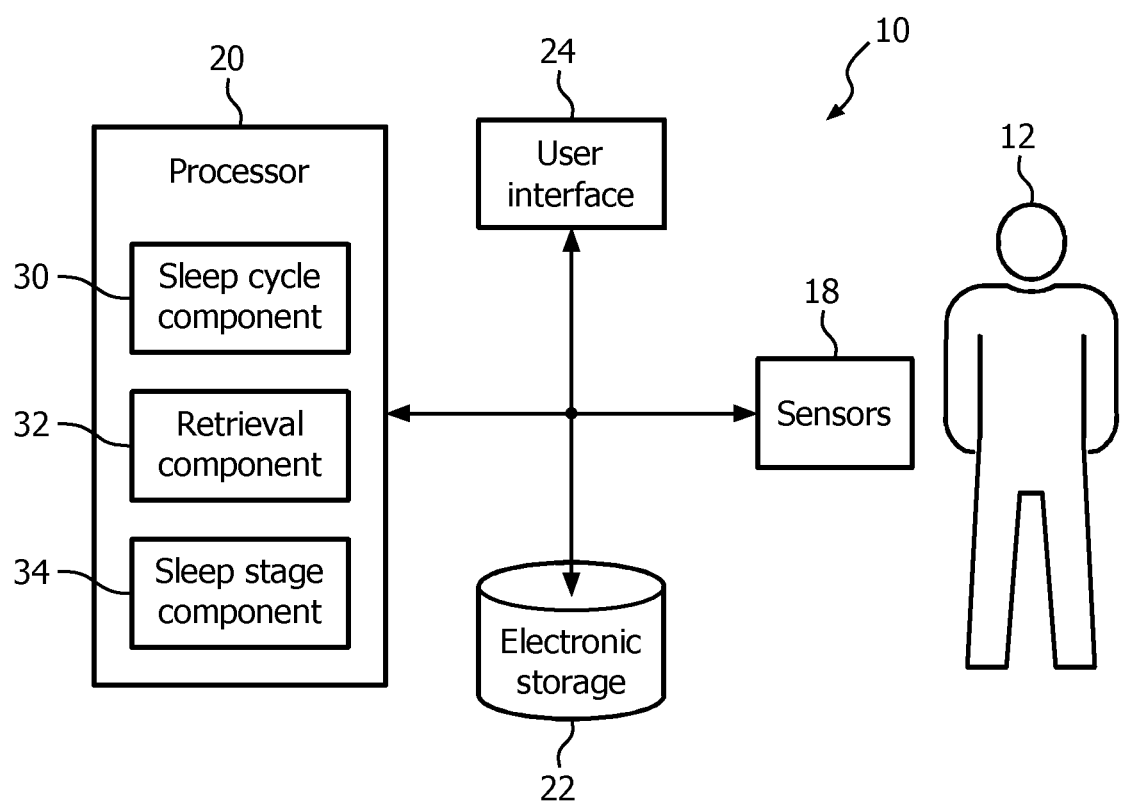
FIG. 1 is a schematic illustration of a system configured to determine sleep stages of a subject during individual sleep cycles of a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine sleep stages of a subject 12 during individual sleep cycles of a sleep session. System 10 enables more accurate real-time sleep stage determinations compared to prior art systems. System 10 determines the current sleep stage of subject 12 based on algorithms and/or parameters that correspond to the current sleep cycle. A sleep cycle corresponds to an orderly progression through successive sleep stages, from light sleep to deep sleep and then followed by rapid eye movement (REM) sleep. Sleep cycles are detected in real-time based on an electroencephalogram (EEG), and/or by other methods. At the end of a sleep cycle, system 10 is configured such that the specific algorithms and/or parameters used for the previous sleep cycle to determine sleep stages are replaced by new ones which are specifically adapted for the next sleep cycle. In some embodiments, system 10 comprises one or more of a sensor 18, a processor 20, electronic storage 22, a user interface 24, and/or other components.

Sensor 18 is configured to generate output signals conveying information related to brain activity of subject 12. The brain activity of subject 12 may correspond to a current sleep cycle, a current sleep stage, and/or other characteristics of subject 12. The brain activity of subject 12 may be associated with rapid eye movement (REM) sleep, non-rapid eye movement (NREM) sleep, and/or other sleep. Sleep stages of subject 12 may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

The output signals generated by sensor 18 may be and/or be related to polysomnography signals. Patterns in polysomnography signals (often the EEG) do not remain stable during a sleep session of subject 12. The EEG exhibits changes throughout a sleep session. The most prominent change is visible in the EEG delta power (also known as slow wave activity (SWA)). Sleep slow waves are associated with SWA in subject 12 during the sleep session. SWA corresponds to the power of an EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated from an EEG for subject 12 during a given sleep session.

Figure 2:
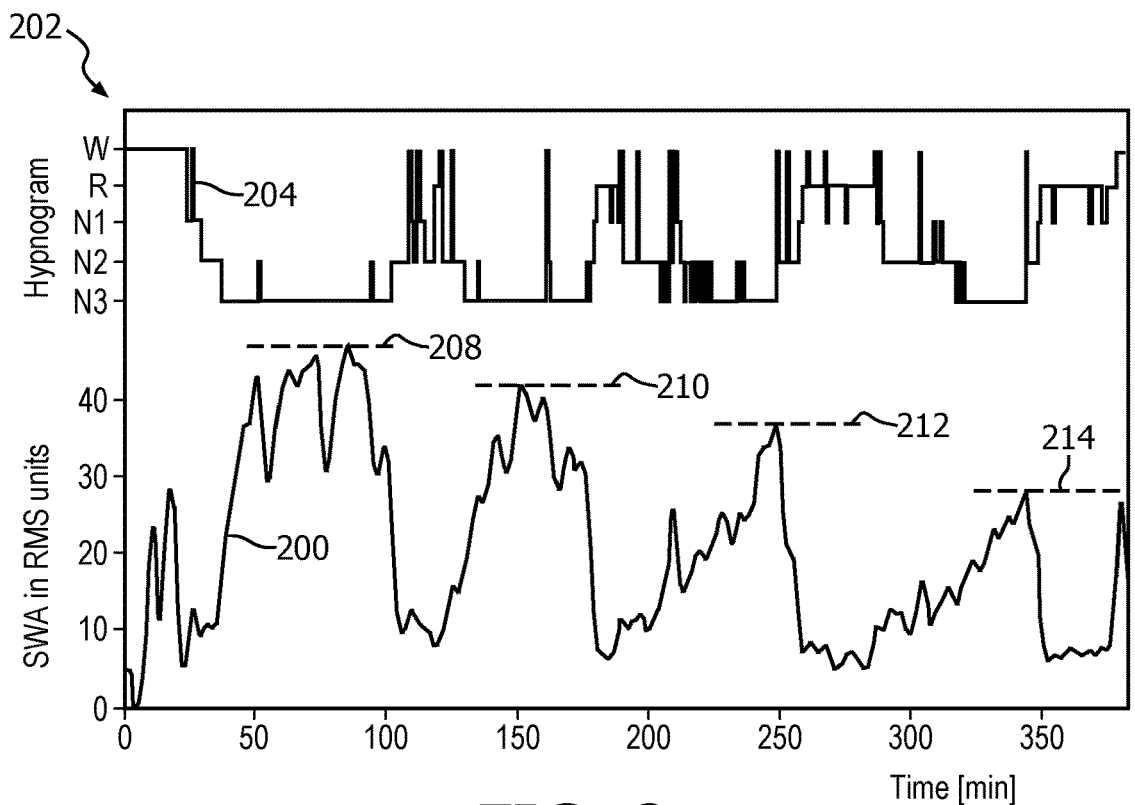
FIG. 2 illustrates cyclical changes in slow wave activity.

FIG. 2 illustrates such cyclical changes in SWA 200. SWA 200 is plotted for an entire sleep session 202. For reference, the corresponding hypnogram 204 is also plotted. SWA 200 progressively decreases 208, 210, 212, and 214 from one NREM episode to the next throughout the sleep session.

Figure 3:
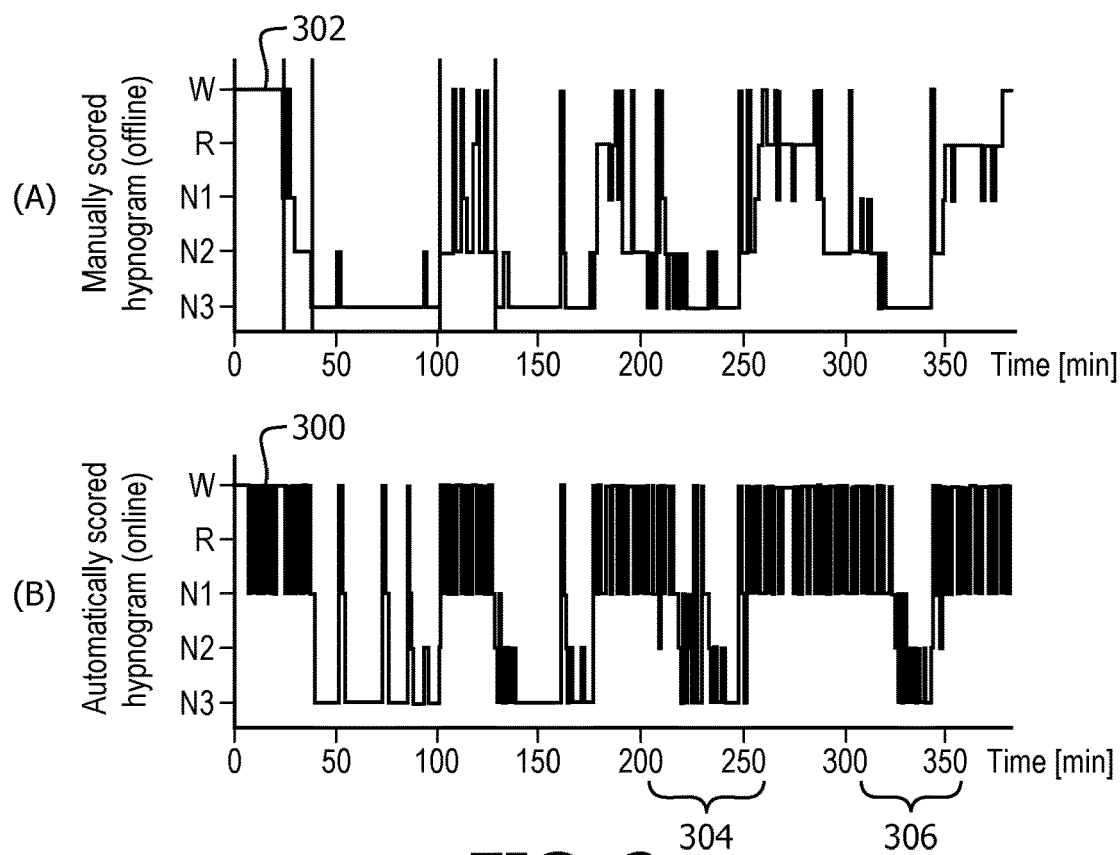
FIG. 3 illustrates how decreasing slow wave activity causes inaccurate sleep stage determinations in prior art systems.

FIG. 3 illustrates how decreasing SWA (shown in FIG. 2) causes inaccurate sleep stage determinations in prior art systems. FIG. 3 illustrates an example of a hypnogram 300 determined based on a static (does not change with sleep cycle) algorithm which applies thresholds on root mean square values of the EEG signal filtered in the delta (0.5 to 4 Hz), alpha (8 to 12 Hz), spindle (11-15 Hz), and beta (15 to 30 Hz) bands. FIG. 3A illustrates a manually scored hypnogram 302 for reference. FIG. 3B illustrates the automatically scored hypnogram 300 using the static algorithm. Ideally, the hypnogram shown in FIG. 3B should closely match the hypnogram shown in FIG. 3A. However, the agreement between the hypnogram in FIG. 3A and the hypnogram in FIG. 3B decreases over time. For instance, for the N3 episode in the third cycle 304 (from 200 to 250 minutes approximately) the algorithm detects too many transitions between N2 and N3. A similar situation can be observed for the N3 episode in the fourth cycle 306 (from 300 to 350 minutes approximately). System 10 (shown in FIG. 1) is configured to minimize and/or eliminate such differences with the manually scored hypnogram, for example. System 10 is configured to base real-time sleep stage determinations on algorithms and/or parameters that correspond to individual sleep cycles and improve the accuracy of the real-time sleep stage determinations.

Returning to FIG. 1, processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensors 18), or processor 20 may represent processing functionality of a plurality of devices operating in coordination.

As shown in FIG. 1, processor 20 is configured to execute one or more computer program components. The one or more computer program components may comprise one or more of a sleep cycle component 30, a retrieval component 32, a sleep stage component 34, and/or other components. Processor 20 may be configured to execute components 30, 32, 34 and/or other components by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, 34, and/or other components may be located remotely from the other components. The description of the functionality provided by the different components 30, 32, 34, and/or other components described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Sleep cycle component 30 is configured to detect individual sleep cycles during the sleep session. Sleep cycle component 30 is configured to detect individual sleep cycles based on the output signals from sensors 18 and/or other information. In some embodiments, detecting individual sleep cycles during the sleep session may include generating and/or monitoring an EEG during a sleep session of subject 12. The EEG may be displayed, for example, by user interface 24. Sleep cycle component 30 is configured to detect the individual sleep cycles based on power in a beta ($\beta$) band of the EEG, power in a delta ($\delta$) band of the EEG, and/or other information. More generally, the ratio between the power in any high frequency band (e.g., alpha [8-12 Hz], beta [15-30 Hz], sigma [11-16 Hz] or gamma [30-60 Hz]) and any low frequency band (e.g., delta [0.5-4 Hz], and theta [4-8 Hz]) may provide a cyclic signal that can be used for sleep cycle detection. The cyclic signal is easily visualized in the ratio of beta/delta (FIG. 2). Yet, one can also observe a cyclic signal if one takes, for example, the ratios alpha/theta, and/or alpha/delta.

In some embodiments, sleep cycle component 30 is configured to detect sleep cycles based on the natural logarithm of the ratio between the EEG powers in the beta and the delta bands (log ($\beta/\delta$)). This ratio may be used because the powers in the delta and beta bands undergo prominent changes (e.g., relative to the power in other bands of the EEG) during cyclical sleep behavior (e.g., shown in FIG. 2). The power in the delta band and the power in the beta band generally exhibit opposite trends (e.g., an increase/decrease in delta is generally mirrored by a decrease/increase in beta).

Figure 4:
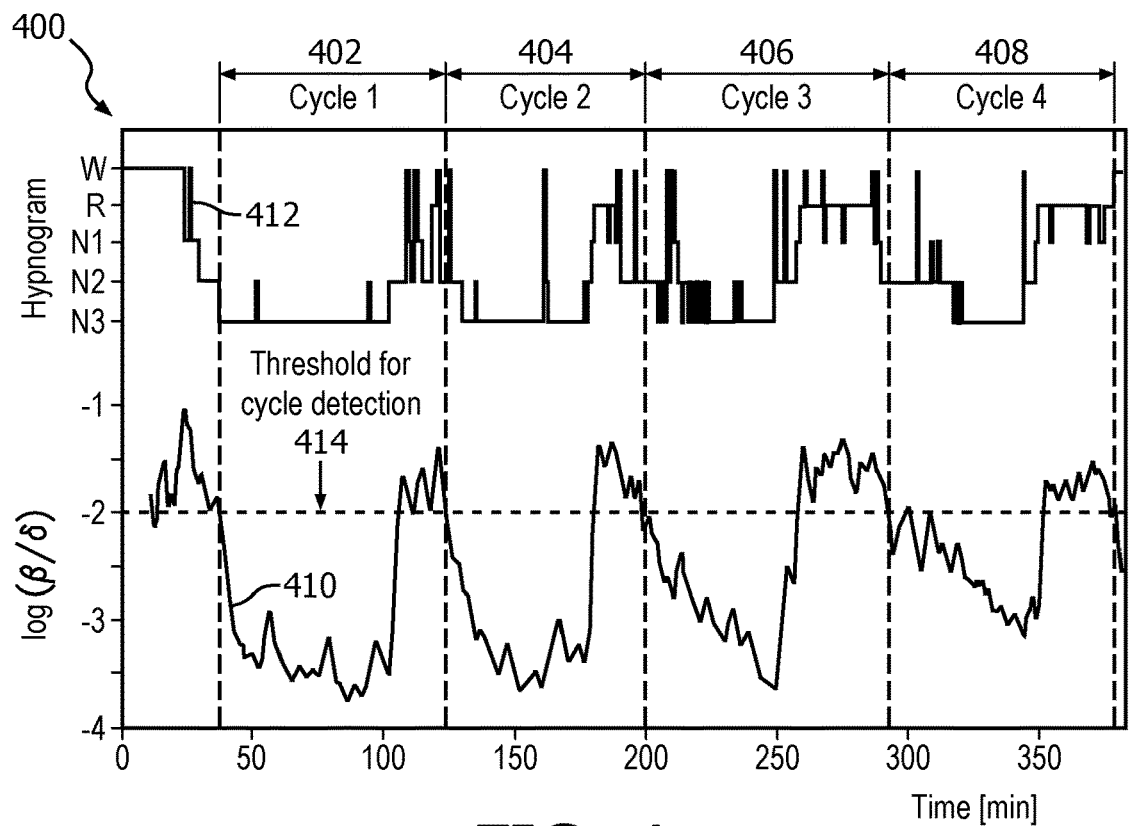
FIG. 4 illustrates four individual sleep cycles detected by a sleep cycle component during a sleep session.

For example, FIG. 4 illustrates four individual sleep cycles 402, 404, 406, 408 detected by sleep cycle component 30 (FIG. 1) during a sleep session 400. In FIG. 4, log ($\beta/\delta$) 410 is plotted below a corresponding manually scored hypnogram 412. In some embodiments, the individual sleep cycles 402, 404, 406, 408 are detected by sleep cycle component 30 based on a log ($\beta/\delta$) threshold 414. In some embodiments, threshold 414 may be determined based on previous sleep sessions of subject 12, and/or other information. In some embodiments, threshold 414 may be set and/or adjusted via user interface 24 (shown in FIG. 1). In some embodiments, threshold 414 may be programmed at manufacture. For example, threshold 414 may be programmed at manufacture based on empirically accepted values such as a threshold of about −2 on the log($\beta/\delta$) (illustrated in FIG. 4). In some embodiments, sleep cycle component 30 is configured to detect individual sleep cycles responsive to log ($\beta/\delta$) 410 breaching log ($\beta/\delta$) threshold 414. In some embodiments, sleep cycle component 30 determines that log ($\beta/\delta$) 410 breaches log ($\beta/\delta$) threshold 414 responsive to log ($\beta/\delta$) 410 staying above and/or below log ($\beta/\delta$) threshold 414 for longer than a given period of time.

It should be noted that the illustration of four individual sleep cycles in FIG. 4 is not intended to be limiting. Subject 12 may experience any number of sleep cycles during a sleep session. System 10 is configured to detect the individual sleep cycles from a first sleep cycle to an $n^{th}$ sleep cycle.

Returning to FIG. 1, retrieval component 32 is configured to obtain predetermined sleep stage detection algorithms, algorithm input parameters, and/or other information that corresponds to different detected sleep cycles. In some embodiments, the predetermined sleep stage detection algorithms, algorithm input parameters, and/or other information is and/or includes sleep stage criteria. The sleep stage criteria may be related to amounts of power in one or more bands of the EEG (e.g., beta, spindle, alpha, theta, delta), and/or related to other characteristics of the brain activity of subject 12. Typical band-limit values are about 8-12 Hz (alpha), about 15-30 Hz (beta), about 11-16 Hz (sigma/spindle), about 30-60 Hz (gamma), about 0.5-4 Hz (delta), and/or about 4-8 Hz (theta).

The sleep stage detection algorithms, parameters, sleep stage criteria, and/or other information for one sleep cycle are different from the sleep stage detection algorithms, parameters, sleep stage criteria, and/or other information for other sleep cycles. In some embodiments, the sleep stage detection algorithms, parameters, sleep stage criteria, and/or other information for one sleep cycle may be similar to and/or the same as the sleep stage detection algorithms, parameters, sleep stage criteria, and/or other information for other sleep cycles.

Non-limiting examples of sleep stage detection algorithms, parameters, sleep stage criteria may include a vector quantization algorithm wherein individual sleep stages are characterized by a representative vector (and/or centroid) and the decision on which stage a given vector (x) belongs to is taken based on the centroid that is closest to the vector "x". The vector "x" may be determined from computing signal processing functions on a segment of EEG signal, for example. A typical duration of the EEG segment is 30 seconds, but this is not intended to be limiting. The signal processing functions include spectral band powers, time domain characterizations such as mean value or entropy, and/or other signal processing functions.

Another example of a sleep stage detection algorithm is a neural network which makes decisions based on a set of features estimated from a portion of the EEG signal for which one wants to know the sleep stage that such an EEG signal portion belongs to.

Yet another example of a sleep stage detection algorithm is a support vector machine, which determines the sleep stage a given vector (x) belongs to by evaluating a generalized scalar product between so-called support vectors and the vector x.

The algorithms mentioned above have parameters that can also change depending on the sleep cycle. For instance, the centroids for individual sleep stages in the vector quantization algorithm can change depending on the sleep cycle. Another example is that of the neural network where the architecture (e.g., the number of layers and/or neurons) may remain the same but the weights can change depending on the sleep cycle. In this example, the algorithm for the first cycle and the second cycle are the same, while the parameters for the first cycle are not the same as the parameters for the second cycle.

In some embodiments, retrieval component 32 is configured to obtain the corresponding predetermined sleep stage detection algorithms, parameters, sleep stage criteria, and/or other information responsive to detection of an individual sleep cycle by sleep cycle component 30. For example, the sleep stage algorithms, parameters, and/or criteria obtained by retrieval component 32 may include first algorithms, parameters, and/or criteria that correspond to a first sleep cycle (e.g., sleep cycle 402 shown in FIG. 4), and second algorithms, parameters, and/or criteria that correspond to a second sleep cycle (e.g., sleep cycle 404 shown in FIG. 4). In some embodiments, retrieval component 32 is configured to obtain one or more individual algorithms, parameters, and/or criteria that correspond to the individual sleep cycle detected by sleep cycle component 30. In some embodiments, retrieval component 32 is configured to obtain one or more sets of algorithms, parameters, and/or criteria that correspond to the individual sleep cycle detected by sleep cycle component 30.

Retrieval component 32 is configured such that the predetermined algorithms, algorithm input parameters, sleep stage criteria, and/or other information are stored electronically (e.g., in electronic storage 22). The predetermined algorithms, algorithm input parameters, sleep stage criteria, and/or other information may be indexed based on the individual sleep cycles. Instead of storing a single algorithm, parameter, and/or set of criteria for a sleep stage, regardless of sleep cycle, system 10 is configured such that several algorithms, parameters, and/or sets of criteria are stored for the various sleep stages that occur during the different sleep cycles. These may be indexed such that, during a first sleep cycle, retrieval component 32 obtains algorithms, parameters, and/or criteria indexed to the first sleep cycle. During a final sleep cycle, retrieval component 32 obtains algorithms, parameters, and/or criteria indexed to the final sleep cycle.

In some embodiments, the predetermined algorithms, algorithm input parameters, criteria, and/or other information are based on one or more of a previous sleep session of subject 12, information from sleep sessions of an age match population of subjects, and/or other information. For example, the sleep stage criteria may be determined using training data (e.g., data from previous sleep sessions) from a pool of users. Alternatively, the sleep stage criteria may be personalized for subject 12 using data from a single and/or multiple baseline (prior) nights of sleep (sleep sessions).

Sleep stage component 34 is configured to determine sleep stages during the different detected sleep cycles. Sleep stage component 34 is configured to determine sleep stages based on the output signals from sensors 18, information from the EEG, the obtained sleep stage detection algorithms, algorithm input parameters, and/or sleep stage criteria for the corresponding sleep cycles, and/or other information. For example, during a first sleep cycle, sleep stages are determined based on the current (e.g., during the first sleep cycle) output signals, current information from the EEG, a first algorithm, a first algorithm input parameter, first sleep stage criteria, and/or other information. The first algorithm, the first algorithm input parameter, and/or the first sleep stage criteria are obtained by retrieval component 32 responsive to sleep cycle component 30 determining that subject 12 is in the first sleep cycle. During a second sleep cycle, sleep stages are determined based on the current (e.g., during the second sleep cycle) output signals, current information from the EEG, a second algorithm, a second algorithm input parameter, and/or second sleep stage criteria.

In some embodiments, sleep stage component 34 is configured to use information conveyed by the output signals, information from the EEG, the obtained algorithm input parameters, and/or other information as algorithm inputs for the obtained algorithms to determine sleep stages in a corresponding sleep cycle. In some embodiments, sleep stage component 34 is configured to determine sleep stages during a given sleep cycle by comparing information conveyed by the output signals, information conveyed by the EEG, and/or other information to the sleep stage criteria for the given sleep cycle.

By way of a non-limiting example, sleep stage component 34 may use the EEG power in five frequency bands (e.g., as described above, delta (0.5 to 4 Hz), theta (4 to 8 Hz), alpha (8 to 12 Hz), spindle (11-16 Hz), and beta (15 to 30 Hz)) to determine the current sleep stage. Sleep stage component 34 may determine the power in the five different frequency bands during one or more fifteen second (for example) long epochs during a sleep session. For an individual epoch, sleep stage component 34 may build a 5-D feature vector based on the power in the five frequency bands. In some embodiments, the 5-D feature vector may be an input into a predetermined algorithm obtained by retrieval component 32 for the current sleep cycle (the algorithm changes depending on the sleep cycle) determined by sleep cycle component 30. In some embodiments, the 5D-feature vector may be compared to sleep stage criteria obtained by retrieval component 32 for the current sleep cycle determined by sleep cycle component 30 (the sleep stage criteria change depending on the sleep cycle). The current sleep stage may be an output of the algorithm and/or or determined responsive to the 5D-feature vector meeting one or more of the sleep stage criteria.

Figure 5:
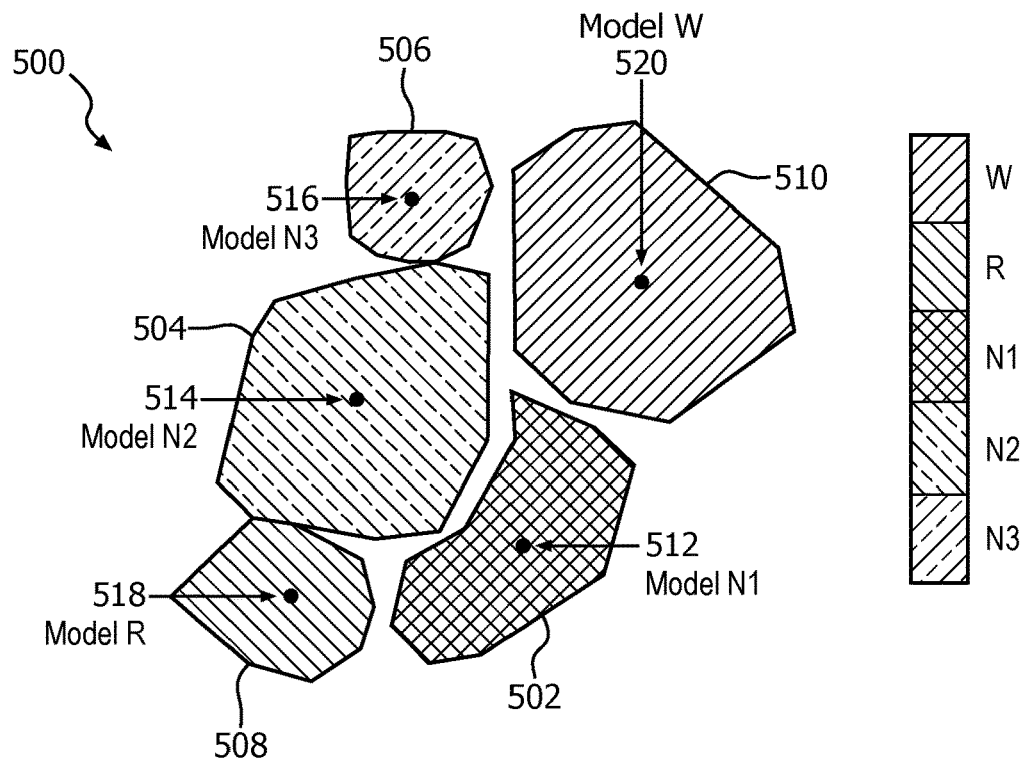
FIG. 5 illustrates a vector quantization approach to determining the current sleep stage.

In this example, the predetermined algorithm obtained by retrieval component 32 is a vector quantization algorithm and/or is related to a vector quantization approach to determining the current sleep stage. Using this approach, feature vectors for training epochs from previous sleep sessions of subject 12 (for which the sleep cycle and the sleep stage are known) are previously determined. Clusters of feature vectors for individual training epochs are used to determine sleep stage feature vector boundaries and/or regions (because the sleep stages for the training epochs are known) that define individual sleep stages in a five-dimensional space (e.g. each dimension corresponding to an EEG power band). The determined sleep stage feature vector boundaries and/or regions vary by sleep cycle. The appropriate set of boundaries and/or regions for the current sleep cycle are obtained by retrieval component 32. Sleep stage component 34 may compare the current 5-D feature vector to the sleep stage feature vector boundaries and/or regions for the current sleep cycle. Sleep stage component 34 may determine the current sleep stage based on the 5-D feature vector and the defined boundaries and/or regions for the current sleep cycle. Apart from the boundaries, one can determine the stage a given vector "x" belongs to by computing the distance between "x" and the centroid of each region. The centroid vector may be defined for individual sleep stages/regions as the center of gravity of the individual region FIG. 5 illustrates the vector quantization approach to determining the current sleep stage. Clusters of known feature vectors from training epochs define regions 502, 504, 506, 508, 510 in a five dimensional space 500 (but illustrated on a 2-D page) that correspond to sleep stages for a given sleep cycle. Representative feature vectors (models) for each sleep stage are indicated by the black dots 512, 514, 516, 518, 520. The representative feature vectors are the centroids (described above), individual centroids being the center of gravity of the corresponding individual regions. To determine which sleep stage a current epoch belongs to, sleep stage component 34 determine the 5-D feature vector from the current epoch based on the power in the five frequency bands of the EEG during the current epoch. Then, sleep stage component 34 compares, through Euclidean distances for example, the 5-D feature vector from the current epoch to each cluster/region to determine in which cluster/region (sleep stage) the current 5-D feature vector is most likely to be located.

Figure 6:
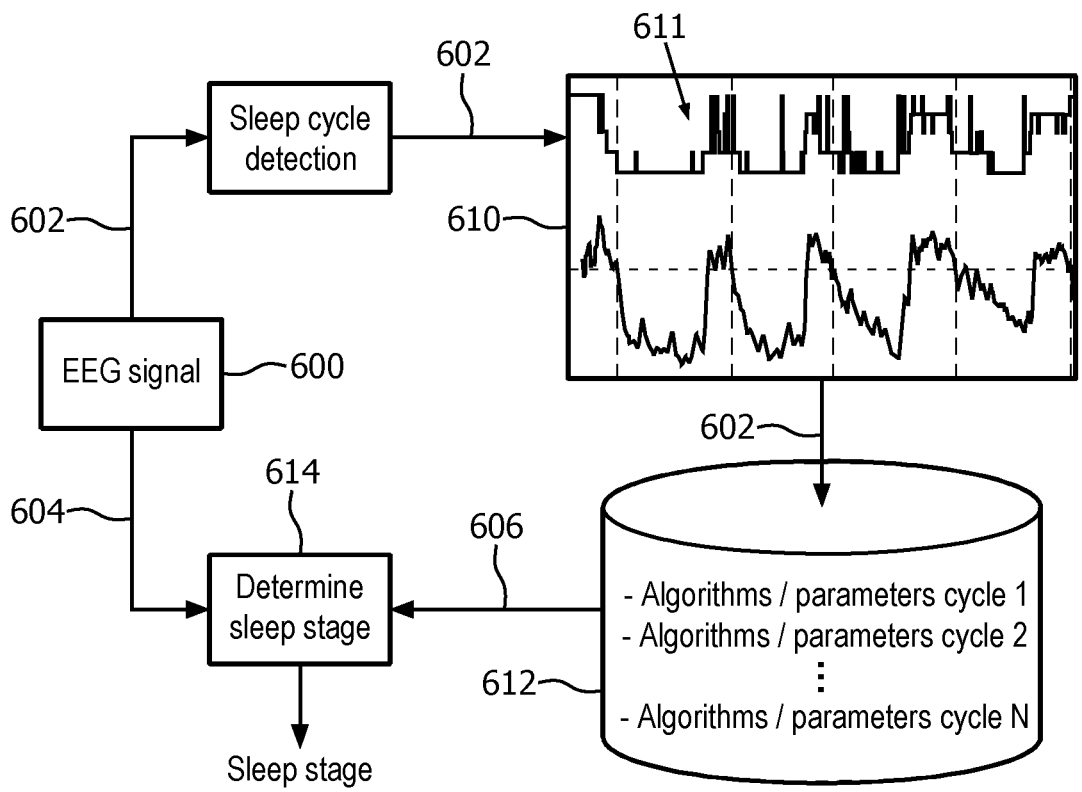
FIG. 6 graphically summarizes real-time sleep stage determinations based on algorithms and/or parameters that correspond to individual sleep cycles.

FIG. 6 graphically summarizes real-time sleep stage determinations based on algorithms and/or parameters that correspond to individual sleep cycles. As shown in FIG. 6, the EEG signal (which is and/or is determined based on the output signals from sensors 18) goes through two sequential and/or substantially simultaneous processes 602, 604. The first process 602 is automatically detecting the sleep cycle. The second process 604 is determining the current sleep stage of subject 12, which receives input 606 from first process 602. The sleep-cycle detection process 602 includes determining the current sleep cycle based on the EEG. A metric derived from the EEG which can be reliably used to determine the sleep cycle is the logarithm of the ratio between the power in the beta (15-30 Hz) band and that in the delta (0.5-4 Hz) band (log ($\beta/\delta$)) of the EEG (reference numeral 610 in FIG. 6., hypnogram 611 is also shown for reference). Sleep cycle component 30 and retrieval component 32 (shown in FIG. 1) detect changes in sleep cycle and retrieve sleep stage determination algorithms and/or parameters indexed to the given sleep cycle. The sleep stage determination algorithms and/or parameters are retrieved from electronic storage 612. Sleep stage determination 614 is based on the EEG signal and the algorithms and/or parameters retrieved from the storage module.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms (e.g., the predetermined algorithms retrieved by retrieval component 32), algorithm inputs (e.g., the predetermined parameters retrieved by retrieval component 32), information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. For example, user interface 24 may display an EEG to a user. This enables data, cues, results, instructions, and/or any other communicable items, collectively referred to as "information," to be communicated between a user (e.g., subject 12, a caregiver, and/or other users) and one or more of sensor 18, processor 20, electronic storage 22, and/or other components of system 10. For example, user interface 24 may facilitate storage of predetermined algorithms and/or parameters in electronic storage 22 by a user.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20, electronic storage 22, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
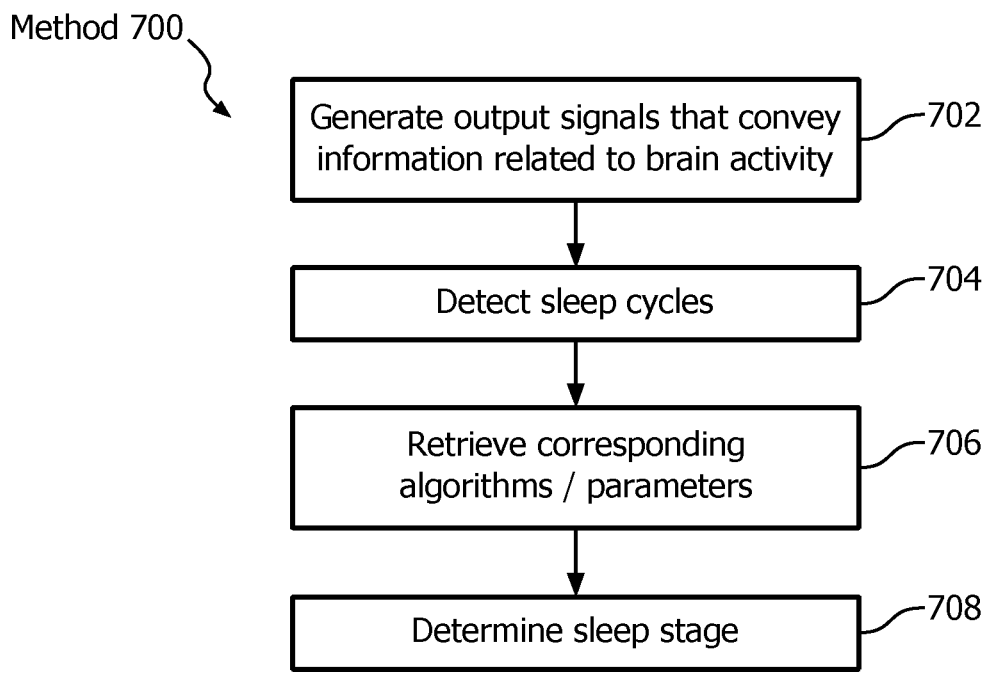
FIG. 7 illustrates a method for determining sleep stages of a subject during individual sleep cycles of a sleep session with a sleep stage determination system.

FIG. 7 illustrates a method 700 for determining sleep stages of a subject during individual sleep cycles of a sleep session with a sleep stage determination system. The system comprises one or more sensors, one or more physical computer processors, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain activity of the subject during a sleep session are generated. In some embodiments, operation 702 is performed by one or more sensors the same as or similar to sensors 18 (shown in FIG. 1 and described herein).

At an operation 704, an individual sleep cycle is detected based on the output signals. In some embodiments, the individual sleep cycle is detected based on power in a beta band and power in a delta band of an EEG, and/or other information. In some embodiments, operation 704 is performed by a physical computer processor component the same as or similar to sleep cycle component 30 (shown in FIG. 1 and described herein).

At an operation 706, predetermined sleep stage determination algorithms, algorithm input parameters, and/or other information that corresponds to the individual sleep cycle detected during operation 704 are retrieved. In some embodiments, the algorithms, algorithm input parameters, and/or other information are retrieved from electronic storage. In some embodiments, the algorithms, algorithm input parameters, and/or other information are indexed in electronic storage based on the individual sleep cycles. In some embodiments, the predetermined algorithms and/or the algorithm input parameters are based on one or more of a previous sleep session of the subject, information from sleep sessions of an age match population of subjects, and/or other information. In some embodiments, operation 706 is performed by a physical computer processor component the same as or similar to retrieval component 32 (shown in FIG. 1 and described herein).

At an operation 708, sleep stages are determined. Sleep stages are determined during different detected sleep cycles. Sleep stages are determined based on the output signals, the obtained sleep stage detection algorithms and/or parameters for the corresponding sleep cycles, and/or other information. For example, during a first sleep cycle, sleep stages are determined based on the output signals, a first algorithm, a first parameter, and/or other information that corresponds to the first sleep cycle. During a second sleep cycle, sleep stages are determined based on the output signals, a second algorithm, a second parameter, and/or other information that corresponds to the second sleep cycle. In some embodiments, operation 708 is performed by a physical computer processor component the same as or similar to sleep stage component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to determine sleep stages of a subject during individual sleep cycles of a sleep session, wherein a sleep cycle comprises multiple sleep stages and corresponds to a progression through the multiple sleep stages from light sleep to deep sleep such that multiple sleep cycles, each comprising the multiple sleep stages, occur throughout a sleep session, the system comprising:

one or more sensors configured to generate output signals conveying information related to brain activity of the subject; and one or more physical computer processors configured by computer-readable instructions to:

store sets of sleep stage detection algorithms and parameters that correspond to different detected sleep cycles, the sets of algorithms and parameters indexed based on respective sleep cycles, the sets of sleep stage algorithms and parameters including a first set of algorithms and parameters that correspond to a first sleep cycle and a second set of algorithms and parameters that correspond to a second sleep cycle;

determine, based on the output signals, power in a beta band and power in a delta band of an electroencephalogram;

detect the individual sleep cycles during the sleep session based on the power in the beta band and the power in the delta band, the individual sleep cycles including the first sleep cycle and the second sleep cycle;

select different ones of the sets of sleep stage detection algorithms and parameters for sleep stage determination during different ones of the detected sleep cycles such that the sets of sleep stage detection algorithms and parameters change between the different ones of the detected sleep cycles, wherein (1)

the first set of algorithms and parameters is selected based on the detection of the first sleep cycle, (ii) the second set of algorithms and parameters is selected based on the detection of the second sleep cycle, (iii) the selected sets of sleep stage detection algorithms and parameters for sleep stage determination during the different ones of the detected sleep cycles are continuously updated as the sleep cycles of the subject progress during a sleep session; and (iv) a selected set of sleep stage detection algorithms and parameters for sleep stage determination does not change as the sleep stages change with a given sleep cycle; and determine the sleep stages during the different ones of the detected sleep cycles based on the output signals and the selected sets of sleep stage detection algorithms and parameters such that the first set of algorithms and parameters are used to determine the sleep stages during the first sleep cycle, and the second set of algorithms and parameters are used to determine the sleep stages during the second sleep cycle.

2. The system of claim 1, wherein the one or more physical computer processors detect the individual sleep cycles based on a log of a ratio between the power in the beta band and the power in the delta band of the electroencephalogram.

3. The system of claim 1, wherein the one or more physical computer processors are further configured such that:

the sets of sleep stage detection algorithms and parameters include vector quantization algorithms, the sleep stages are characterized by representative centroids in a multi-dimensional vector space, the representative centroids comprising a first representative centroid and a second representative centroid, the representative centroids change based on the sleep cycle, and the sleep stages are determined during the different detected sleep cycles based on the output signals and the representative centroids such that, during the first sleep cycle, the sleep stages are determined based on the output signals and the first representative centroid, wherein the first representative centroid is closest to a first current sleep stage vector, and, during the second sleep cycle, the sleep stages are determined based on the output signals and the second representative centroid, wherein said second representative centroid is closest to a second current sleep stage vector.

4. The system of claim 1, wherein the one or more physical computer processors are configured such that the sets of algorithms and parameters are determined based on information from sleep sessions of an age match population of subjects.

5. The system of claim 1, wherein the one or more physical computer processors are configured such that storing the sets of sleep stage detection algorithms and parameters that correspond to the different ones of the detected sleep cycles comprises storing sets of sleep stage vectors and centroids of a multi-dimensional vector space, the sleep stage vectors and centroids corresponding to the different detected sleep cycles, the sets of sleep stage vectors and centroids indexed based on the individual sleep cycles, the sets of sleep stage vectors and centroids including a first set of sleep stage vectors and centroids that correspond to the first sleep cycle and a second set of sleep stage vectors and centroids that correspond to the second sleep cycle, such that, during the first sleep cycle, the sleep stages are determined based on the output signals and the first set of sleep stage vectors and centroids, and, during the second sleep cycle, the sleep stages are determined based on the output signals and the second set of sleep stage vectors and centroids.

6. A method for determining sleep stages of a subject during individual sleep cycles of a sleep session with a sleep stage determination system, wherein a sleep cycle comprises multiple sleep stages and corresponds to a progression through the multiple sleep stages from light sleep to deep sleep such that multiple sleep cycles, each comprising the multiple sleep stages, occur throughout a sleep session, and wherein the system comprises one or more sensors and one or more physical computer processors, the method comprising:

generating, with the one or more sensors, output signals conveying information related to brain activity of the subject;

storing, with the one or more physical computer processors, sets of sleep stage detection algorithms and parameters that correspond to different detected sleep cycles, the sets of algorithms and parameters indexed based on the individual sleep cycles, the sets of sleep stage algorithms and parameters including a first set of algorithms and parameters that correspond to a first sleep cycle and a second set of algorithms and parameters that correspond to a second sleep cycle;

determining, with the one or more physical computer processors, based on the output signals, power in a beta band and power in a delta band of an electroencephalogram;

detecting, with the one or more physical computer processors, the individual sleep cycles during the sleep session based on the power in the beta band and the power in the delta band, the individual sleep cycles including the first sleep cycle and the second sleep cycle;

selecting, with the one or more physical computer processors, different ones of the sets of the sleep stage detection algorithms and parameters for sleep stage determination during different ones of the detected sleep cycles, such that the sets of sleep stage detection algorithms and parameters change between different ones of the detected sleep cycles, wherein (i) the first set of algorithms and parameters is selected based on the detection of the first sleep cycle, (ii) the second set of algorithms and parameters is selected based on the detection of the second sleep cycle, (iii) the selected sets of sleep stage detection algorithms and parameters for sleep stage determination during different ones of the detected sleep cycles are continuously updated as the sleep cycles of the subject progress during a sleep session, and (iv) a selected set of sleep stage detection algorithms and parameters for sleep stage determination does not change as the sleep stages change with a given sleep cycle; and determining, with the one or more physical computer processors, the sleep stages during different ones of the detected sleep cycles based on the output signals and the selected sets of sleep stage detection algorithms and parameters such that the first set of algorithms and parameters are used to determine the sleep stages during the first sleep cycle, and the second set of algorithms and parameters are used to determine the sleep stages during the second sleep cycle.

7. The method of claim 6, wherein the individual sleep cycles are detected based on a log of a ratio between the power in the beta band and the power in the delta band of the electroencephalogram.

8. The method of claim 6, wherein:
the sets of sleep stage detection algorithms and parameters include vector quantization algorithms,
the sleep stages are characterized by representative centroids in a multi-dimensional vector space, the representative centroids comprising a first representative centroid and a second representative centroid,
the representative centroids change based on the sleep cycle, and
the sleep stages are determined during the different detected sleep cycles based on the output signals and the representative centroids such that, during the first sleep cycle, the sleep stages are determined based on the output signals and the first representative centroid, wherein the first representative centroid is closest to a first current sleep stage vector, and, during the second sleep cycle, the sleep stages are determined based on the output signals and the second representative centroid, wherein said second representative centroid is closest to a second current sleep stage vector.

9. The method of claim 6, wherein the sets of algorithms and parameters are determined based on information from sleep sessions of an age match population of subjects.

10. The method of claim 6, wherein storing the sets of sleep stage detection algorithms and parameters that correspond to the different detected sleep cycles comprises storing sets of sleep stage vectors and centroids of a multi-dimensional vector space, the sleep stage vectors and centroids corresponding to the different detected sleep cycles, the sets of sleep stage vectors and centroids indexed based on the individual sleep cycles, the sets of sleep stage vectors and centroids including a first set of sleep stage vectors and centroids that correspond to the first sleep cycle and a second set of sleep stage vectors and centroids that correspond to the second sleep cycle, such that, during the first sleep cycle, the sleep stages are determined based on the output signals and the first set of sleep stage vectors and centroids, and, during the second sleep cycle, the sleep stages are determined based on the output signals and the second set of sleep stage vectors and centroids.

11. A system configured to determine sleep stages of a subject during individual sleep cycles of a sleep session, wherein a sleep cycle comprises multiple sleep stages and corresponds to a progression through the multiple sleep stages from light sleep to deep sleep such that multiple sleep cycles, each comprising the multiple sleep stages, occur throughout a sleep session, the system comprising:
means for generating output signals conveying information related to brain activity of the subject;
means for storing sets of sleep stage vectors and centroids of a multi-dimensional vector space, the sleep stage vectors and centroids corresponding to different detected sleep cycles, the sets of sleep stage vectors and centroids indexed based on the individual sleep cycles, the sets of sleep stage vectors and centroids including a first set of sleep stage vectors and centroids that correspond to a first sleep cycle and a second set of sleep stage vectors and centroids that correspond to a second sleep cycle;
means for detecting, based on the output signals, power in a beta band and power in a delta band of an electroencephalogram;
means for detecting the individual sleep cycles during the sleep session based on the power in the beta band and the power in the delta band, the individual sleep cycles including the first sleep cycle and the second sleep cycle;
means for selecting different ones of the sets of sleep stage vectors and centroids for sleep stage determination during different ones of the detected sleep cycles, such that the sets of sleep stage vectors and centroids change between different ones of the detected sleep cycles, wherein (i) the first set of sleep stage vectors and centroids is selected based on a detection of the first sleep cycle, (ii) the second set of sleep stage vectors and centroids is selected based on a detection of the second sleep cycle, (iii) the selected sets of sleep stage detection algorithms and parameters for sleep stage determination during different ones of the detected sleep cycles are continuously updated as the sleep cycles of the subject progress during a sleep session, and (iv) a selected set of sleep stage detection algorithms and parameters for sleep stage determination does not change as the sleep stages change with a given sleep cycle; and
means for determining the sleep stages during different ones of the detected sleep cycles based on the output signals and the selected sets of sleep stage vectors and centroids such that the first set of sleep stage vectors and centroids are used to determine the sleep stages during the first sleep cycle, and the second set of sleep stage vectors and centroids are used to determine the sleep stages during the second sleep cycle.

12. The system of claim 11, wherein the means for detecting detects the individual sleep cycles based on a log of a ratio between the power in beta band and the power in the delta band of the electroencephalogram.

13. The system of claim 11, wherein the means for determining sleep stages is configured such that: the sleep stages are characterized by one or more of a representative vector or a representative centroid, and a decision on which sleep stage a given current sleep stage vector belongs to is taken based on a representative vector or a representative centroid that is closest to the given current sleep stage vector for a corresponding sleep cycle.

14. The system of claim 11, wherein the sleep stage vectors and centroids are determined based on information from sleep sessions of an age match population of subjects.

* * * * *